United States Patent
Cox et al.

(10) Patent No.: US 8,486,012 B1
(45) Date of Patent: *Jul. 16, 2013

(54) APPARATUS TO PREVENT REPERFUSION INJURY

(75) Inventors: Daniel L. Cox, Palo Alto, CA (US);
Hongzhi Bai, Menlo Park, CA (US);
Paul Consigny, San Jose, CA (US);
Jessica G. Chiu, Belmont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/571,110

(22) Filed: Aug. 9, 2012

Related U.S. Application Data

(60) Continuation of application No. 12/943,879, filed on Nov. 10, 2010, now Pat. No. 8,262,612, which is a division of application No. 11/026,598, filed on Dec. 30, 2004, now Pat. No. 7,837,650.

(51) Int. Cl.
*A61M 25/10* (2006.01)
*A61M 31/00* (2006.01)

(52) U.S. Cl.
USPC .............. 604/102.01; 604/509; 604/510

(58) Field of Classification Search
USPC ............ 604/96.01, 101.01, 101.04, 101.05, 604/102.01, 102.02, 102.03
See application file for complete search history.

(56) References Cited

U.S. PATENT DOCUMENTS

| | | |
|---|---|---|
| 5,158,548 A | 10/1992 | Lau et al. |
| 5,648,331 A | 7/1997 | Koudsi et al. |
| 5,653,689 A | 8/1997 | Buelna et al. |
| 5,797,876 A | 8/1998 | Spears et al. |
| 5,925,016 A | 7/1999 | Chornensky et al. |
| 5,935,122 A | 8/1999 | Fourkas et al. |
| 6,022,336 A | 2/2000 | Zadno-Azizi et al. |
| 6,044,845 A | 4/2000 | Lewis |
| 6,231,588 B1 | 5/2001 | Zadno-Azizi |
| 6,235,007 B1 | 5/2001 | Divino, Jr. et al. |
| 6,309,379 B1 | 10/2001 | Willard et al. |
| 6,435,189 B1 | 8/2002 | Lewis et al. |
| 6,436,087 B1 | 8/2002 | Lewis et al. |
| 6,481,439 B1 | 11/2002 | Lewis et al. |
| 6,599,283 B1 | 7/2003 | Marzilli et al. |
| 6,660,034 B1 | 12/2003 | Mandrusov et al. |
| 6,666,880 B1 | 12/2003 | Chiu et al. |
| 6,783,541 B2 | 8/2004 | Stephens et al. |
| 6,905,476 B2 | 6/2005 | Ponzi |
| 7,008,411 B1 | 3/2006 | Mandrusov et al. |
| 7,326,195 B2 | 2/2008 | Willard et al. |
| 2002/0132845 A1 | 9/2002 | Miller et al. |
| 2002/0169436 A1 | 11/2002 | Gurn et al. |
| 2003/0022870 A1 | 1/2003 | Dzau et al. |

(Continued)

OTHER PUBLICATIONS

Abbott Cardiovascular Systems, Non Final Office Action dated Jun. 11, 2009 for U.S. Appl. No. 11/026,598.

(Continued)

*Primary Examiner* — Aarti B Berdichevsky

(74) *Attorney, Agent, or Firm* — Blakely Sokoloff Taylor & Zafman LLP

(57) ABSTRACT

Embodiments of a method and apparatus to prevent reperfusion injury. In one embodiment, blood flow proximal to a lesion is occluded. An infusion catheter is advanced to a region distal to the lesion and an anti-reperfusion injury drug is delivered. The lesion may then be treated with a dilating device to reintroduce blood flow to the region distal to the lesion.

15 Claims, 9 Drawing Sheets

U.S. PATENT DOCUMENTS

| | | |
|---|---|---|
| 2005/0015048 A1 | 1/2005 | Chiu et al. |
| 2005/0107741 A1 | 5/2005 | Willard et al. |
| 2006/0265043 A1 | 11/2006 | Mandrusov et al. |
| 2007/0208297 A1 | 9/2007 | Ainsworth et al. |

OTHER PUBLICATIONS

Abbott Cardiovascular Systems, Final office action dated Oct. 16, 2009 for U.S. Appl. No. 11/026,598.

Abbott Cardiovascular Systems, Non final office action dated Mar. 30, 2010 for U.S. Appl. No. 11/026,598.

Abbott Cardiovascular Systems, Non-final Office Action mailed Aug. 4, 2011 for U.S. Appl. No. 12/943,879., 15 pages.

Abbott Cardiovascular Systems, Final Office Action mailed Feb. 2, 2012 for U.S. Appl. No. 12/943,879., 8 pages.

Assmus, B., et al., "Transplantation of Progenitor Cells and Regeneration Enhancement in Acute Myocardial Infarction (TOPCARE-AMI)", *Clinical Investigation and Reports*, Circulation, 106, (2002), 3009-3017.

Mandrusov, "Membrane-based Cell Affinity Chromatography to Retrieve Viable Cells, Biotechnol", Prob. 1995, 11, 208-213, *Artificial Organs Research Laboratory, Department of Chemical Engineering, Material Science and Metallurgy*, Columbia UNiversity, New York, New York 10027, and Louisville, Louisville, Kentucky 40292.

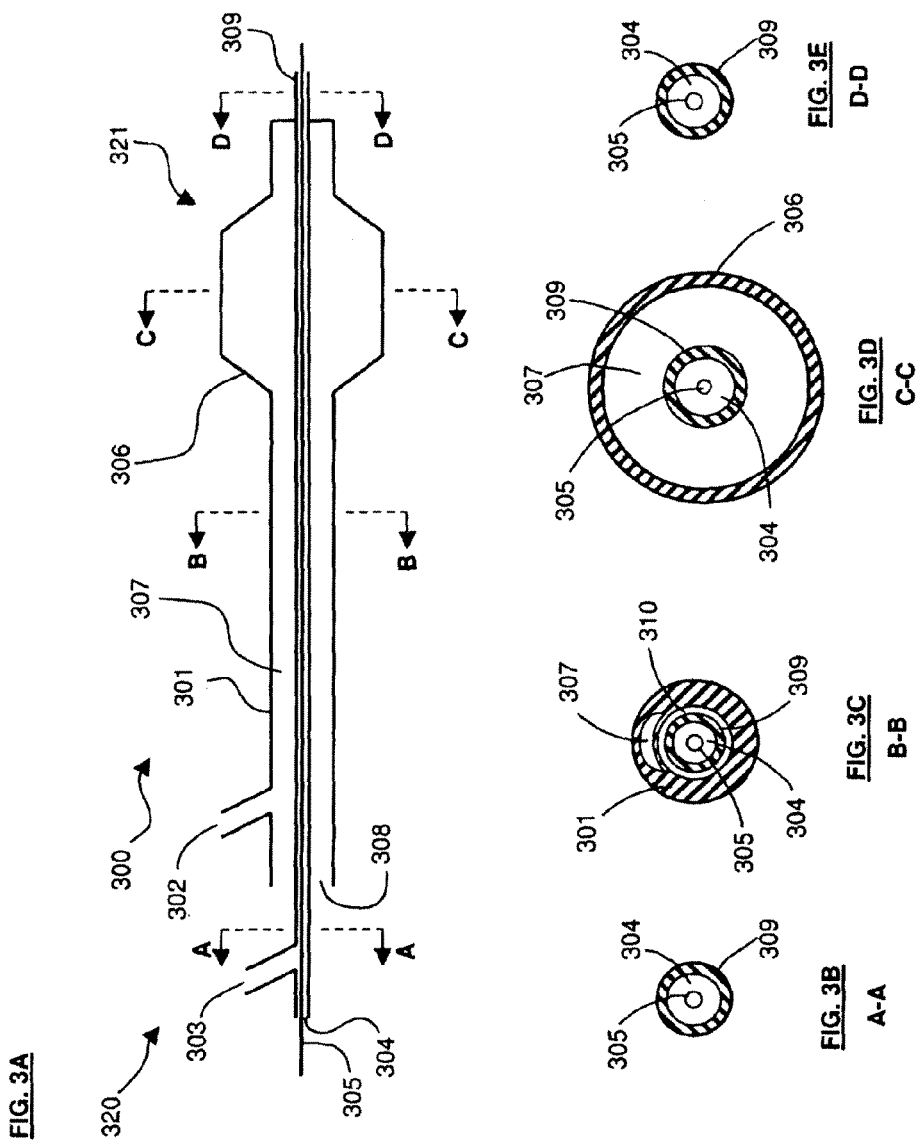

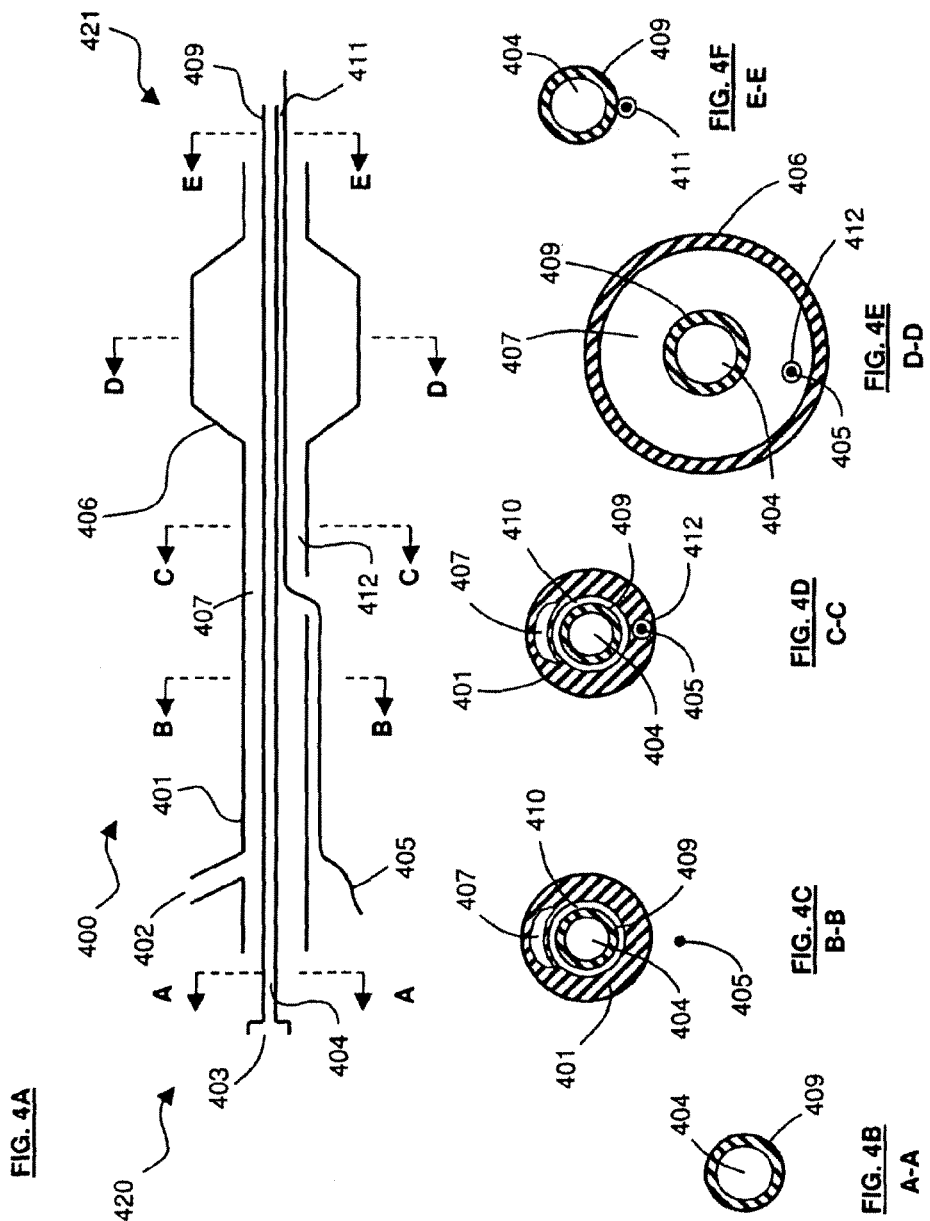

APPARATUS TO PREVENT REPERFUSION INJURY

CROSS-REFERENCE TO RELATED APPLICATION

This application is a continuation of pending U.S. patent application Ser. No. 12/943,879 filed Nov. 10, 2010 issued as U.S. Pat. No. 8,262,612 on Sep. 11, 2012 which is a divisional of U.S. patent application Ser. No. 11/026,598 filed Dec. 30, 2004, entitled "METHOD AND APPARATUS TO PREVENT REPERFUSION INJURY" and issued as U.S. Pat. No. 7,837,650 on Nov. 23, 2010.

TECHNICAL FIELD

The disclosure, in one embodiment, relates generally to the treatment of heart related diseases, and more particularly, in one embodiment, to the prevention of reperfusion injury after a reperfusion procedure to re-establish blood flow to an ischemic region of an artery.

BACKGROUND

Cardiac ischemia is a situation in which the blood flow inside a coronary artery is restricted by a partial or complete blockage. As a result, the heart cannot get enough oxygen-rich blood. The blockage within the coronary artery, which supplies the heart with oxygen-rich blood, may be complete or partial. The most common cause of cardiac ischemia is plaque build-up in the arteries due to the long-term effects of coronary artery disease. This plaque build-up narrows the arteries to the point where the amount of blood flowing through the arteries is not enough for the heart during times of physical exertion or emotional stress.

Reperfusion by vascular intervention (e.g., angioplasty) has become the standard therapy for coronary artery disease. A substantial subset of patients undertaken with timely revascularization, however, still fails to salvage myocardium especially under the condition of emerging ischemia such as acute myocardial infarction and unstable angina. In particular, the cells distal to the blockage continue to degrade in a process known as "reperfusion injury", even after blood flow is restored. This unfavorable outcome stems from a discrepancy between an open epicardial infarct-related artery and the absence of blood flow in the damaged distal microvasculatures. In fact, studies have shown that even after patients undergo successful revascularization by angioplasty and recover normal epicardial blood flow, a significant number of these patients failed to attain full recovery of microvascular flow. Thus, "myocardial perfusion" is the ultimate goal of reperfusion therapy, which reflects the distribution of blood at the capillary and tissue level.

Research projects have been proposed and undertaken to mitigate reperfusion injury after myocardial ischemia in large animal experiments as well as clinical trials with using various biochemical compounds. In animal studies, the drugs are typically administered prior to induction of ischemia in order to determine the overall benefits. In contrast, clinical settings do not allow the administration of the drug prior to ischemia except for preventive therapy. Thus, the difference in the timing of drug administration can be one of the major reasons why all the previous clinical trials aiming to prevent reperfusion injury have failed in spite of significant positive results in the animal experiments.

In the clinical trials, systemic intra-venous administration has been commonly used, and the method of intra-coronary infusion soon after successful revascularization has also been attempted. However, because reperfusion injury is triggered by reperfusion therapy, and supposedly ignites a series of biological responses in a very immediate, rapid manner, these systemic methods would be too late for the delivery of an anti-reperfusion injury agent to the ischemic lesion and are likely to miss the critical time-window for the therapy. The systemic or intra-coronary administration of an anti-reperfusion injury agent will not allow the agent to reach the ischemic area prior to reperfusion. In order to address reperfusion injury within the critical time window, a local therapy system that enables drug delivery under the absence of blood flow (ischemic condition) is needed.

SUMMARY

Embodiments of a method and apparatus to prevent reperfusion injury are described. In one embodiment, blood flow proximal to a lesion is occluded. An infusion catheter is advanced to a region distal to the lesion and an anti-reperfusion injury drug is delivered. The lesion may then be treated with a dilating device to reintroduce blood flow to the region distal to the lesion.

In one embodiment, a percutaneous device includes an elongated catheter having a proximal region and a distal region, within expandable member coupled to the elongated catheter near the distal region. An infusion catheter is disposed within a first lumen formed within the elongated catheter, and the infusion catheter is slideable within the first lumen to extend a substantial length past the distal region of the elongated catheter. The infusion catheter may be adapted to release an anti-reperfusion drug.

Additional embodiments, features and advantages of the medical device will be apparent from the accompanying drawings, and from the detailed description that follows below.

SUMMARY

Embodiments of a method and apparatus to prevent reperfusion injury are described. In one embodiment, blood flow proximal to a lesion is occluded. An infusion catheter is advanced to a region distal to the lesion and an anti-reperfusion injury drug is delivered. The lesion may then be treated with a dilating device to reintroduce blood flow to the region distal to the lesion. In another embodiment, a medical device includes an elongated catheter having a proximal region and a distal region, an expandable member coupled to the elongated catheter near the distal region and an infusion catheter disposed within a first lumen formed within the elongated catheter. The infusion catheter is slideable within the first lumen to extend a substantial length past the distal region of the elongated catheter to release an anti-reperfusion drug.

There are numerous other embodiments which are described herein, and these embodiments generally relate to the prevention of reperfusion injury.

BRIEF DESCRIPTION OF THE DRAWINGS

The present disclosure is illustrated by way of example, and not limitation, in the figures of the accompanying drawings in which:

FIG. 3A is a cross-sectional, side view of one embodiment of a medical device that may be used to prevent reperfusion injury.

FIG. 3B is a cross-sectional view of the device shown in FIG. 3A taken along line A-A.

FIG. 3C is a cross-sectional view of the device shown in FIG. 3A taken along line B-B.

FIG. 3D is a cross-sectional view of the device shown in FIG. 3A taken along line C-C.

FIG. 3E is a cross-sectional view of the device shown in FIG. 3A taken along line D-D.

FIG. 4A is a cross-sectional, side view of another embodiment of a medical device that may be used to prevent reperfusion injury.

FIG. 4B is a cross-sectional view of the device shown in FIG. 4A taken along line A-A.

FIG. 4C is a cross-sectional view of the device shown in FIG. 4A taken along line B-B.

FIG. 4D is a cross-sectional view of the device shown in FIG. 4A taken along line C-C.

FIG. 4E is a cross-sectional view of the device shown in FIG. 4A taken along line D-D.

FIG. 4F is a cross-sectional view of the device shown in FIG. 4A taken along line E-E.

DETAILED DESCRIPTION

In the following description, numerous specific details are set forth such as examples of specific materials or components in order to provide a thorough understanding of the present disclosure. It will be apparent, however, to one skilled in the art that these specific details need not be employed to practice the disclosure. In other instances, well known components or methods have not been described in detail in order to avoid unnecessarily obscuring the present disclosure. Embodiments of a medical device discussed below are described with respect to the treatment of cardiac ischemia caused by the blockage of blood flow from lesions within an arterial vessel. It may be appreciated, however, that other blood vessels or channels in the body may be treated, and embodiments of the medical device are not limited in their applicability to treat coronary arteries.

Figure 1A:
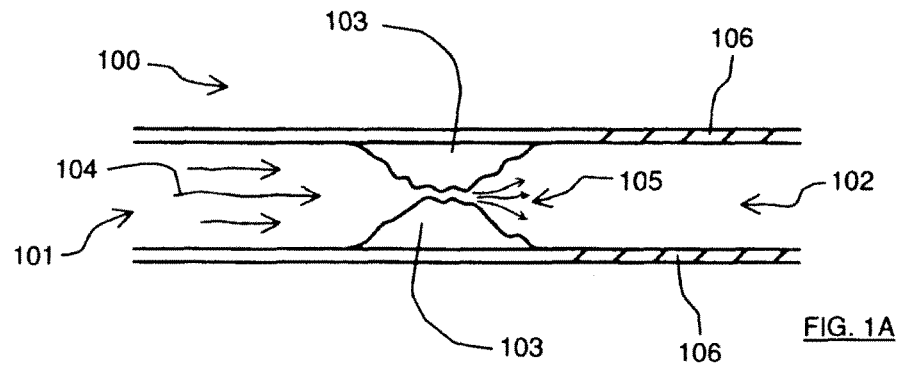
FIG. 1A illustrates a cross-sectional view of an arterial vessel whose blood flow is impacted by the occlusive nature of a lesion.
Figure 1B:
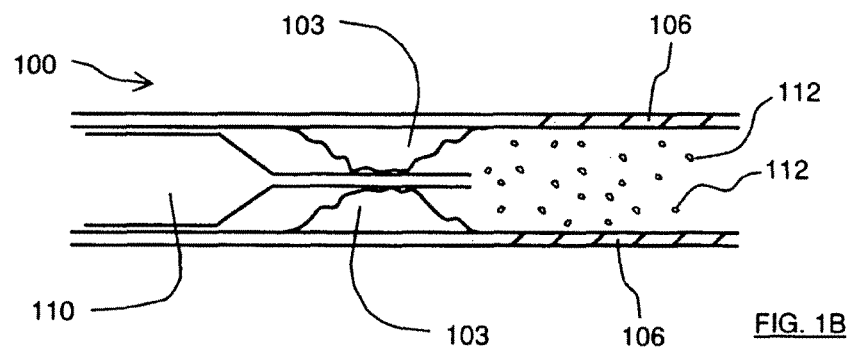
FIG. 1B illustrates the expansion of a balloon catheter to occlude blood flow near a region proximal to the lesion.
Figure 1C:
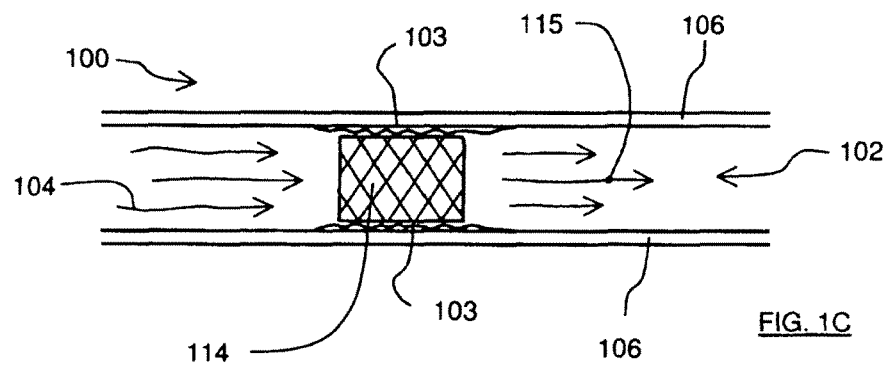
FIG. 1C illustrates a balloon-expandable stent deployed near lesion to reperfuse the arterial vessel.
Figure 2:
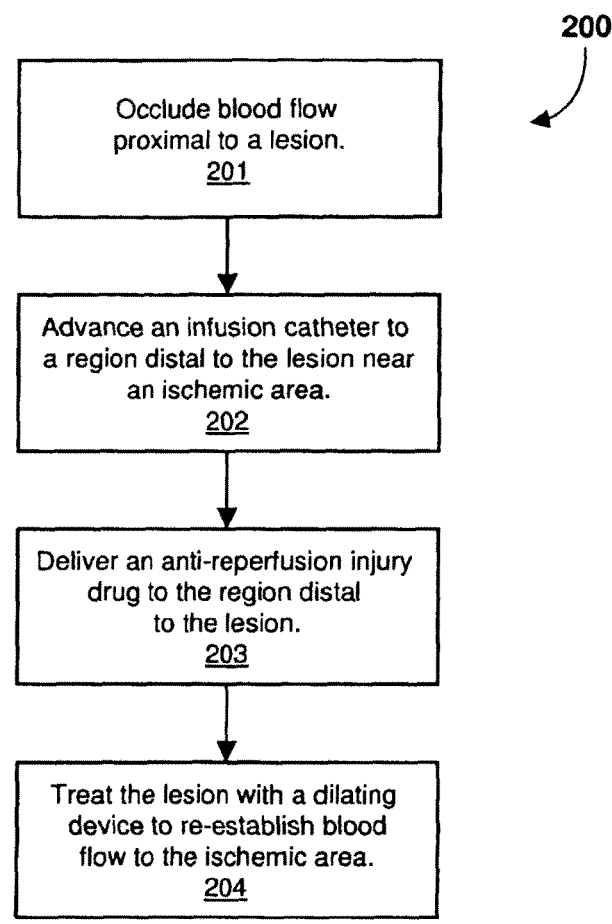
FIG. 2 is a block diagram that generally describes one embodiment of a method to prevent reperfusion injury.

Embodiments of a medical device and methods for preventing reperfusion injury are described. FIGS. 1A-1C and the block diagram 200 of FIG. 2, taken together, generally describe one embodiment of preventing reperfusion injury with a percutaneous drug delivery device. FIG. 1A illustrates a cross-sectional view of an arterial vessel 100 whose blood flow is impacted by the occlusive nature of lesion 103 (i.e., plaque accumulation). As shown, the relatively normal blood flow 104 near the region proximal 101 to lesion 103 is significantly blocked near the region distal 102 to lesion 103, producing very little blood flow 105 downstream to lesion 103. The lack of oxygenated blood to distal region 105 results in ischemic conditions (generically represented by reference 106), potentially resulting in a myocardial infarction. One method to re-establish blood flow to distal region 102 may be the application of a reperfusion procedure. In one embodiment, a dilatation device (e.g., as part of an angioplasty procedure) may be used to treat lesion 103, such as the application of a balloon catheter or a stent to lesion 103.

In one embodiment, the ischemic region 106 may be treated with a drug to prevent reperfusion injury. In particular, an anti-reperfusion injury drug is allowed to be absorbed into the arterial walls of the ischemic region prior to re-establish blood flow past lesion 103. In order to maximize the effectiveness of the anti-reperfusion injury drug to ischemic region 106, blood flow past lesion 103 is blocked. The treatment of ischemic region 106 with an anti-reperfusion injury drug first involves occluding blood flow near the region proximal 101 to lesion 103 (block 201). As illustrated in FIG. 1B, a balloon catheter 110 (or other occlusive device) may be inflated (or otherwise radially expanded) near the proximal region 101 to occlude blood flow 104. Balloon catheter 110 also includes an infusion catheter portion that is advanced past lesion 103 to the distal region 103 (block 202). The infusion catheter is used to deliver an anti-reperfusion injury drug 112 to the ischemic region 106 of arterial vessel 100 (block 203). The infusion catheter along with balloon catheter 110 is then retracted from arterial vessel 100, allowing for lesion 103 to be treated with a dilating device to re-establish blood flow to ischemic region 106 (block 204). As illustrated in FIG. 1C, a balloon-expandable stent or a self-expanding stent may be deployed to lesion 103 to reperfuse arterial vessel 100 distal to lesion 103. For clarity, this embodiment, and other embodiments presented herein, are described with respect to the prevention of reperfusion injury to arterial vessels. It may be appreciated however, that in other embodiments, other vessels in the body (e.g., peripheral) impacted by lesions or other forms of blockage may be treated for reperfusion injury with the apparatus and methods described herein.

FIGS. 3A-3E illustrate detailed views of one embodiment of a medical device for the percutaneous delivery of an anti-reperfusion injury drug to an ischemic region (e.g., an arterial vessel region distal to an occlusive lesion). FIG. 3A is a cross-sectional, side view of the medical device 300 (e.g., a balloon catheter) that includes an elongated catheter body 301 with a proximal portion 320 and a distal portion 321.

Proximal portion includes a first lumen 308 to receive infusion catheter 309. Infusion catheter 309 includes at least one infusion port 303, and in one embodiment, may be a Y-adapter. The inner wall of infusion catheter 309 forms a second lumen 304 to receive guidewire 305. Proximal portion 320 also includes an infusion port for infusion catheter 309.

Distal portion 321 of medical device 300 includes an expandable member 306 coupled to elongated catheter body 301. In one embodiment, expandable member 306 may be an inflatable balloon. Inflatable balloons with respect to catheters are known in the art; accordingly, a detailed description is not provided herein. Infusion catheter 309 extends through expandable member 306 to expose a distal tip portion. Guidewire 305 may also extend out past a distal tip portion of infusion catheter 309. In an alternative embodiment, guidewire 305 may include pressure and/or flow transducers that to monitor the blood pressure, blood flow, blood velocity, vascular resistance and/or vascular conductance. First port 302 leads to first lumen 307 for the insertion of an inflation medium for expandable member 306. Infusion port 303 leads to second lumen 304 for the passage of a therapeutic drug (e.g., an anti-reperfusion injury drug) to be released from distal portion 321 of infusion catheter 309. Infusion catheter 309 is generally described to refer to any type of percutaneous catheter structure adapted for the delivery of therapeutic agents into a body vessel. Device 300 is an exemplary embodiment of an over-the-wire ("OTW") catheter in which elongated catheter body 301 and/or infusion catheter 309 is tracked over guidewire 305. As such, guidewire 305 extends along an entire length of device 300.

FIGS. 3B-3E illustrate various cross-sectional views of medical device 300. FIG. 3B in particular, is a cross-sectional view of device 300 taken along line A-A illustrating the body of infusion catheter 309 forming second lumen 304 to receive guidewire 305 near proximal portion 320. FIG. 3C is a cross-sectional view of device 300 taken along line B-B illustrating elongated catheter body 301 forming first lumen 307 for the passage of an inflation medium from port 302 to expandable member 306. Catheter body 301 also forms a third lumen 310 to receive infusion catheter 309 which contains guidewire 305 within second lumen 304. FIG. 3D is a cross-sectional view of device 300 taken along line C-C (through expandable member 306) showing first lumen 307 formed by expandable member 306, as well as infusion catheter 309 containing guidewire 305 within second lumen 304. Lastly, FIG. 3E is a cross-sectional view of device 300 taken along line D-D (near distal portion 321) of infusion catheter 309 containing guidewire 305 within second lumen 304.

In one embodiment, one of the significant features of medical device 300 is the mobility of infusion catheter 309 within elongated catheter body 301. Guidewire 305 and infusion catheter 309 may move independently with respect to each other, as well as to elongated catheter body 301. That is, infusion catheter 309 is slideable within third lumen 310 to extend beyond a distal section of expandable member 306. As described in greater detail below, this feature allows infusion catheter 309 to traverse toward a region distal to a lesion and deliver an anti-reperfusion injury drug to a portion of the arterial vessel, while the stationary expandable member 306 maintains blockage of blood flow in the region proximal to the lesion. The application of an anti-reperfusion injury drug prior to reperfusion treatment of the lesion may be important because a period of time is allowed for the drug to infuse into the arterial wall and take effect. If blood flow were re-established about the same time as delivering the anti-reperfusion injury drug, the drug may not effectively be absorbed by the arterial wall. In one embodiment, a diameter of infusion catheter 309 is sized to be small enough to advance across an occlusive arterial lesion without causing a large channel or reperfusion pathway from forming.

In one embodiment, a distal section of infusion catheter 309, which is to be positioned downstream of a lesion, has a profile that is relatively small or smaller than the section of infusion catheter 309 which is near or spans across the lesion. For example, infusion catheter 309 may have a tapered diameter that gradually reduces in size near the distal section.

FIGS. 4A-4F illustrate detailed views of another embodiment of a medical device 400 for the delivery of an anti-reperfusion injury drug to an arterial vessel. Device 400 includes similar structural elements as device 300 described above with respect to FIG. 3A including an elongated catheter body 401, a proximal portion 420 with a port 402 and a distal portion 421 with an expandable member 406. The proximal and distal skirts of expandable member 406 may be attached to exterior surface of catheter body 401. A Y-adapter having a port 402 may be in fluid communication with inflation lumen 407 that is defined by catheter body 401, which extends from the proximal end of the catheter to a point proximal to the catheter distal end, and which is in fluid communication with an inflatable interior of expandable member 406. Port 402 may be configured for attaching to an inflation fluid source or medium (not shown in FIG. 4). In one embodiment, port 402 may be a luer lock or a luer lock-type of fitting to couple to a syringe containing an inflation medium. An infusion catheter 409 is disposed within elongated catheter body 401, and may extend from proximal portion 420 and past expandable member 406 near distal portion 421. Infusion catheter 409 forms a first lumen 404 for delivering a therapeutic drug towards the distal end, and the proximal end may include an infusion port 403 to couple with a syringe or other device containing anti-reperfusion injury drug. In one embodiment, infusion port 403 may include a luer lock or a luer lock-type of coupling mechanism.

One significant difference between device 400 and device 300 is the configuration of guidewire 405 with respect to infusion catheter 409. In device 400, guidewire 405 does not extend throughout an entire length of infusion catheter 409. Instead, guidewire 405 extends externally along an outer wall of elongated catheter from proximal portion 420 and enters elongated catheter body 401 near expandable member 406. A guidewire lumen 412 is formed within elongated catheter body 401 near the distal portion 421 to receive guidewire 405, and guidewire 405 also extends towards a guide member 411 that is coupled near the distal tip of infusion catheter 409. Device 400 may be referred to as a "rapid exchange" ("RX") catheter device because guidewire 405 is not inserted from a proximal portion of elongated catheter body 401 and threaded throughout its entire length towards distal portion 421.

FIGS. 4B-4F illustrate various cross-sectional views of medical device 400. For example, FIG. 4B shows a cross-sectional view taken along line A-A near proximal portion 420 which includes infusion catheter 409 forming first lumen 404 for passing an anti-reperfusion injury drug along the elongated catheter body 401. FIG. 4C shows a cross-sectional view taken along line B-B of elongated catheter body 401. Inflation lumen 407 is formed extending from port 402 and second lumen 410 is formed to receive infusion catheter 409. FIG. 4D shows a cross-sectional view of device 400 taken along line C-C which includes one additional lumen formed by elongated catheter body 401. Inflation lumen 407 is formed within one section of elongated catheter body 401 which eventually lead to expandable member 406. Second lumen 410 is also formed by elongated catheter body 401 to receive infusion catheter 409. As described above, infusion catheter 409 includes infusion lumen 404. This portion of device 400 also includes guidewire lumen 412 to receive guidewire 405. FIG. 4E shows a cross-sectional view of device 400 taken along line D-D (through expandable member 406) showing inflation lumen 407 formed by expandable member 406, as well as infusion catheter 409 forming infusion lumen 404. This section also includes guidewire 405 disposed within guidewire lumen 412. Lastly, FIG. 4F is a cross-sectional view of device 400 taken along line E-E (near distal portion 421) of infusion catheter 409 coupled to guide 411 which supports guidewire 405. It should be noted that FIGS. 3A-3E and FIGS. 4A-4F illustrate an embodiment of the catheter shaft that may be formed by a multi-lumen extrusion process (i.e., formed by extruding a single tube with multiple lumens defined by the tube wall). In an alternative embodiment, the multiple lumens may be defined by separate coaxial or side-by-side tubular members.

Figure 5A:
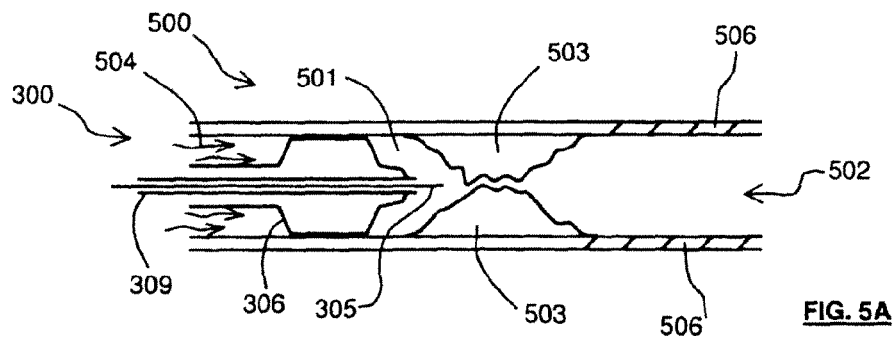
FIG. 5A illustrates a cross-sectional, side view of an expandable member that occludes blood flow near a region proximal to a lesion formed within an arterial vessel.

The effective administration of the anti-reperfusion injury drug may depend on an environment that is free from blood flow (i.e., blood flow may "wash" the drug further downstream than intended, preventing absorption into the arterial wall). The sequence of events illustrated in FIGS. 5A-5F and the block diagram 600 of FIG. 6, taken together, show one detailed embodiment of a method to prevent reperfusion injury using medical device 300 described above with respect to FIGS. 3A-3E. The reperfusion procedure, in one embodiment, is a procedure prior to a direct treatment of a lesion with a balloon or stent (e.g., angioplasty or stent delivery to the lesion). FIG. 5A illustrates a cross-sectional, side view of arterial vessel 500 containing a lesion 503 causing blockage of blood flow 504 from a region proximal 501 to lesion 503 to a region distal 502 to lesion 503. As described in greater detail above, the region distal 502 to lesion 503 is generally represented as the ischemic region 506 of arterial vessel 500. Device 300 is advanced within arterial lumen 500 to a position proximal 501 to lesion 503. In one embodiment, guidewire 305 may first be percutaneously introduced into the cardiovascular system of a patient through the brachial or femoral arteries and advanced through the vasculature until the distal end of the guidewire 305 is positioned near the region proximal 501 to lesion 503.

Figure 5B:
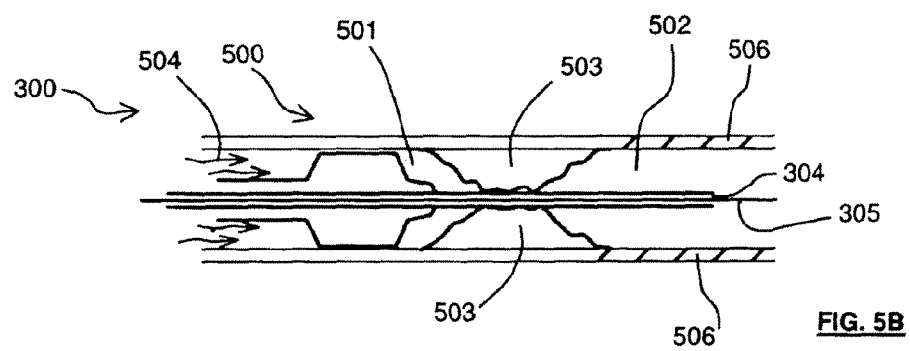
FIG. 5B illustrates a guidewire advanced to a region distal to a lesion.
Figure 6:
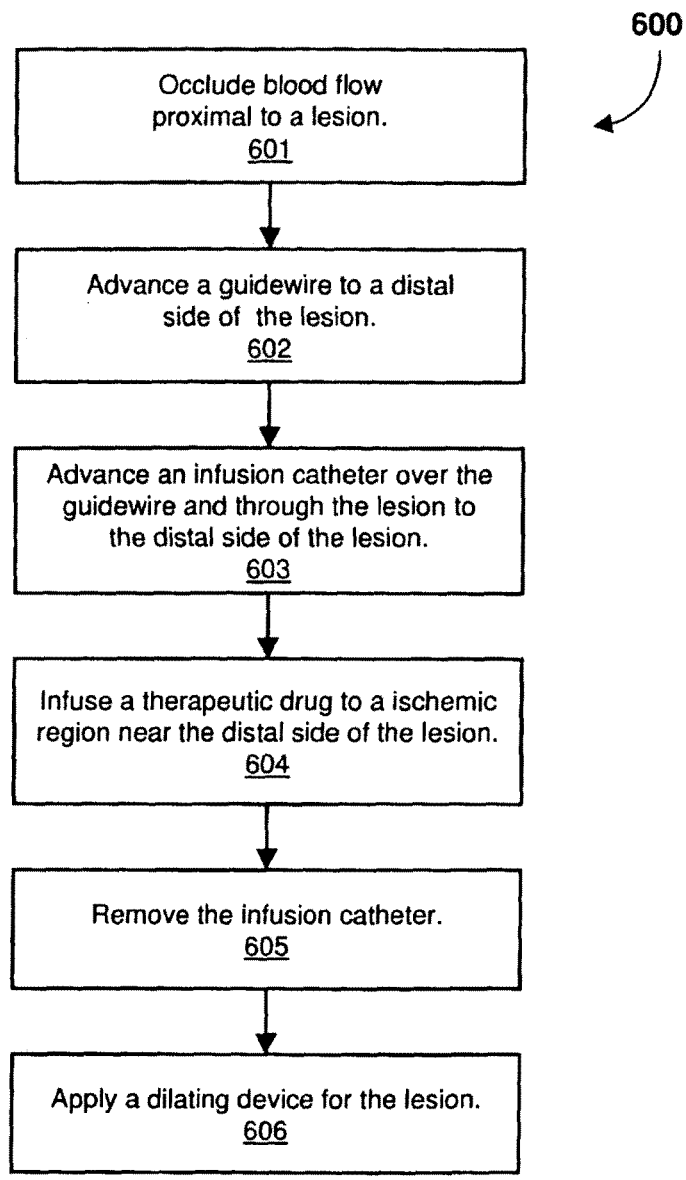
FIG. 6 is a block diagram illustrating another method for the prevention of reperfusion injury.

Elongated catheter body 301, including expandable member 306 and infusion catheter 309 is tracked over guidewire 305 and also positioned near the region proximal 501 to lesion 503. Expandable member 306 of device 300 is inflated, as shown in FIG. 5A, in order to occlude blood flow 504 in the region proximal 501 to lesion 503, block 601. As shown in FIG. 5B, guidewire 305 is advanced in a distal direction past lesion 503 to the region distal 502 of lesion 503 by threading through lumen 304 of infusion catheter 309, block 602. In one embodiment, infusion catheter 309 of device 300 may also be advanced to the region distal 502 to lesion 503, block 603. Infusion catheter 309 is slideable within a lumen 310 formed within elongated catheter body 301.

Figure 5C:
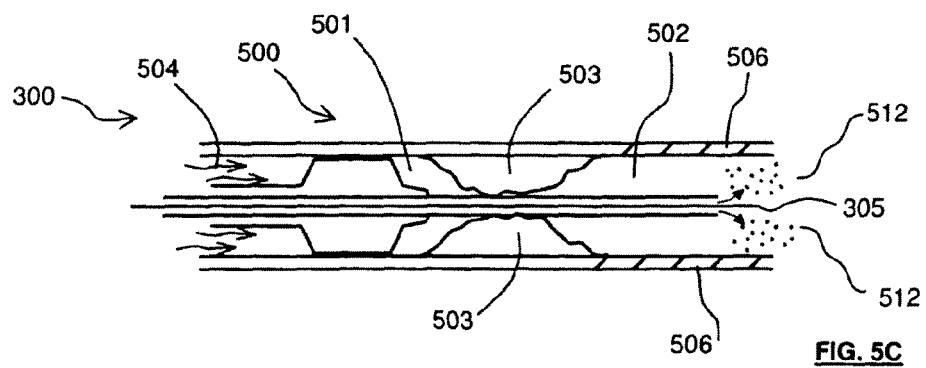
FIG. 5C illustrates an anti-reperfusion injury drug released from an infusion catheter.
Figure 5D:
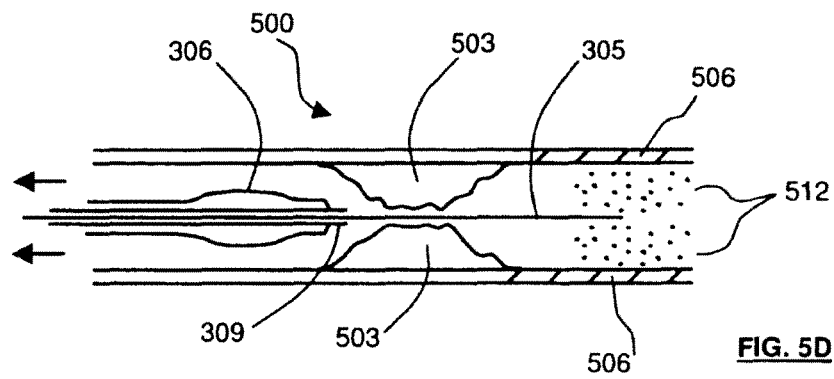
FIG. 5D illustrates the expandable member of a device in a deflated state to allow for the removal of the device from the arterial lumen.

Next, as illustrated in FIG. 5C, an anti-reperfusion injury drug 512 is released from infusion catheter 309 into the region distal 502 to lesion 503. In one embodiment, anti-reperfusion injury drug 512 is released from lumen 304 formed by infusion catheter 309. Anti-reperfusion injury drug 512 is allowed to infuse to ischemic region 506 of arterial vessel 500, block 604. After a period of time as determined by the physician or device operator, infusion catheter 309 is removed from distal region 502 and withdrawn from arterial lumen 500 while guidewire 305 remains distal to lesion 503, block 605. As illustrated in FIG. 5D, expandable member 306 is deflated to allow for the removal of device 300 from arterial lumen 500. In one embodiment, occlusion of blood flow by expandable member 306 may be allowed to continue for a specified period of time even after the delivery of anti-reperfusion injury drug 512. This allows for the drug to infuse sufficiently into the arterial wall near ischemic region 506 for maximum effectiveness.

Figure 5E:
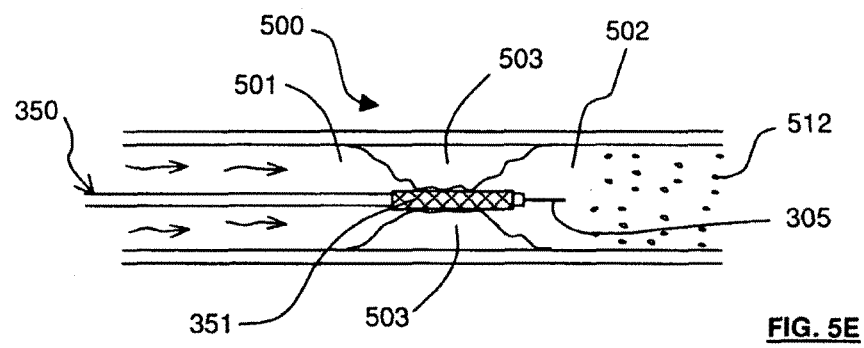
FIG. 5E illustrates a separate catheter device having an expandable stent disposed near a distal end advanced through arterial lumen and positioned near the lesion.
Figure 5F:
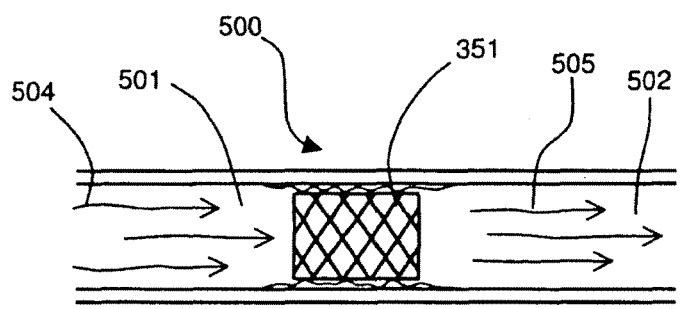
FIG. 5F illustrates a seperate catheter device having an expanded stent.

After the delivery of anti-reperfusion injury drug 512, a dilating or reperfusion device may be applied to lesion 503, block 606. As illustrated in FIG. 5E, a separate catheter device 350, having an expandable stent 351 disposed near a distal end is advanced over guidewire 305 through arterial lumen 500 and positioned near lesion 503. Prior to deployment, stent 351 of device 350 is shown in a contracted state positioned near lesion 503. Stent 351 may then be deployed from device 350 and allowed to expand (either through balloon expansion or self expansion) to clear the blockage caused by lesion 503, and re-establish blood flow from the region proximal 501 to lesion 503 to the region distal 502. For a self-expanding stent, a sheath may be initially disposed over the stent to maintain it in a contracted state (e.g., as shown in FIG. 5E). The sheath (not shown) may then be removed to allow the stent to self-expand. The normal blood flow from the region proximal 501 is generally represented by arrows 504 and the normal blood flow in the region distal 502 to lesion 503 is generally represented by arrows 505 (e.g. as shown in FIG. 5F). As such, the treatment of an ischemic region with an anti-reperfusion injury drug prior to establishing blood flow prevents the occurrence of reperfusion injury.

In an alternative method, expandable member 306 may be used for the reperfusion procedure. That is, instead of substituting device 350 after the removal of device 300, expandable member 306 of device 300 may be advanced distally toward lesion 503 and inflated. This alternative avoids the need for a second catheter device to perform the reperfusion procedure, allowing for a reduction in treatment time and cost. In another embodiment, a double-balloon catheter (not shown) may be used to provide a combination of drug delivery and dilation treatment. For example, the catheter may include a first proximal balloon and a second distal balloon. The double balloon catheter is disposed near a lesion so that the first proximal balloon is proximal to the lesion and the second distal balloon is near the lesion. The first proximal balloon may first be inflated to occlude blood flow proximal to the lesion. An infusion catheter or guidewire disposed within the catheter may be advanced distal to the lesion and an anti-reperfusion drug released. After a period of time for the drug to take effect, the second distal balloon may be inflated to treat the lesion, and subsequently deflated to reperfuse blood flow past the lesion.

In another embodiment, anti-reperfusion injury drug 512 may be delivered without advancing infusion catheter 309 past lesion 503. For example, guidewire 305 is advanced past lesion 503 toward ischemic region 506 (e.g., as illustrated in FIG. 5D). If lesion 503 were larger than shown, guidewire 305 may generate a hole through lesion 503, but not large enough to cause significant blood flow from the proximal side. As such, an expandable member would not be required to occlude blood flow proximal to lesion 503. The anti-reperfusion injury drug 512 would then be released from a lumen defined by guidewire 305.

In one embodiment, on-time, in-situ recovery of vascular/microvascular flow may be assessed as part of the anti-reperfusion injury therapy. The parameters that may be used for this assessment include blood pressure, flow velocity, flow volume, vascular resistance, vascular conductance, oxygen content in arterial and/or venous blood, the difference of arterial and venous oxygen content, and a combination of these parameters. In addition to flow reserve, biochemical markers, for example inflammatory response markers such as II-1b, and white blood cell content and activity markers such as myeloperoxidase activity and LDH can be used to assess the degree of reperfusion injury, if any.

Figure 7A:
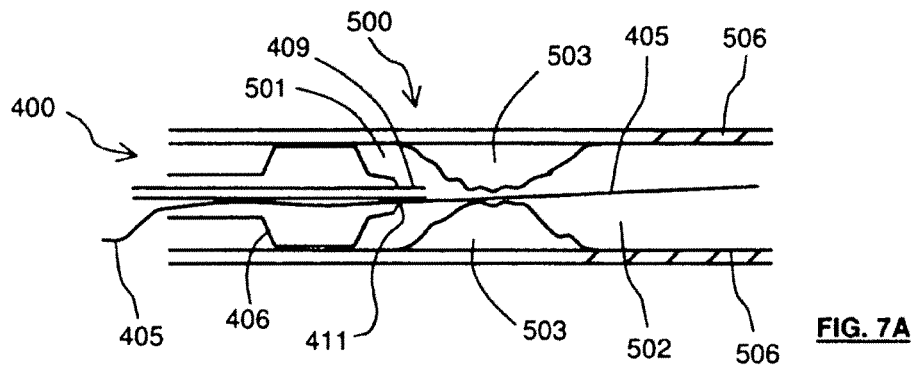
FIG. 7A illustrates another cross-sectional, side view of an expandable member occluding blood flow near a region proximal to a lesion formed within an arterial vessel.
Figure 7B:
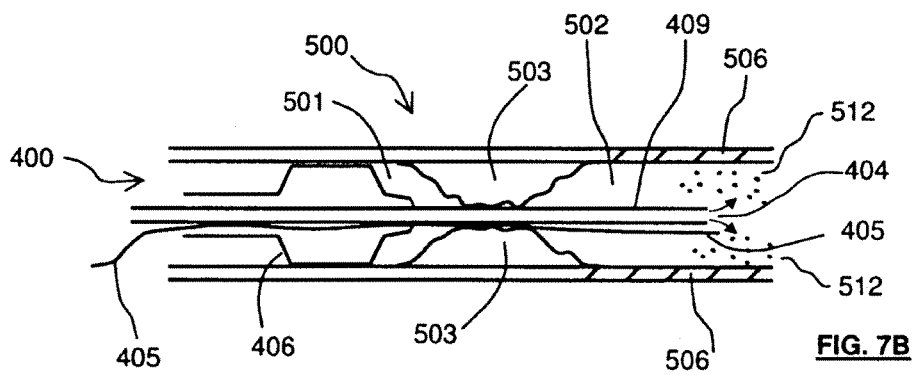
FIG. 7B illustrates an infusion catheter advanced past the lesion along the guidewire.
Figure 7C:
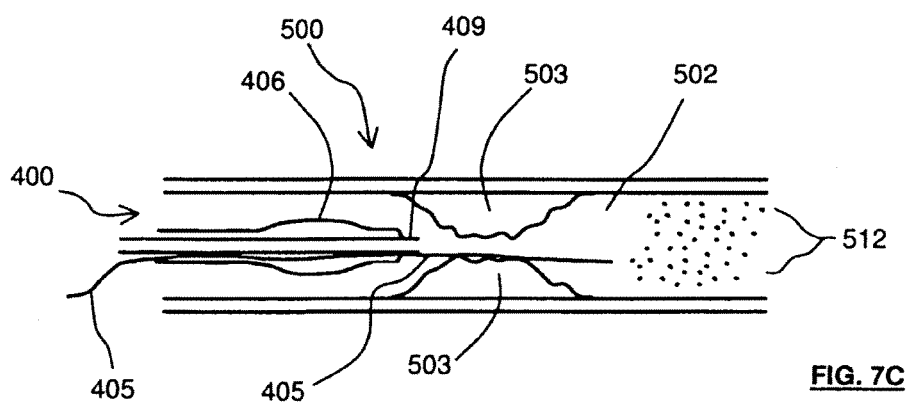
FIG. 7C illustrates the deflation of the expandable member for the removal of the device.

FIGS. 7A-7C illustrate another treatment sequence for the delivery of an anti-reperfusion injury drug to an ischemic region of an arterial vessel, in which device 400 described above with respect to FIGS. 4A-4F is used. FIG. 7A illustrates device 400 advanced within arterial lumen 500 to a position proximal 501 to lesion 503. Blood flow towards lesion 503 has been occluded by the inflation of expandable member 406 to occupy a substantial portion of the diameter of arterial vessel 500. In one embodiment, expandable member 406 may be an inflatable balloon. Device 400 reflects a "rapid exchange" configuration for guidewire 405 in which only a distal portion of device 400 tracks over guidewire 405, instead of guidewire 405 advanced through an entire length of elongated catheter body 401. Guidewire 405 is inserted within elongated catheter 401 through expandable member 406 and anchored to infusion catheter 409 with guide 411. Once blood flow has been occluded by expandable member 406, guidewire 405 is advanced past lesion 403 to distal region 502 (i.e., near ischemic region 506).

Next, as illustrated in FIG. 7B, infusion catheter 409 is advanced past lesion 503 along guidewire 405 to distal region 502. Once in position, the anti-reperfusion injury drug 512 is released from the distal tip of infusion catheter 409 for absorption by the arterial wall of ischemic region 506. After delivery of anti-reperfusion injury drug 512, infusion catheter 409 is retracted back across lesion 503, followed by guidewire 405. Expandable member 406 is deflated and device 400 may then be removed from arterial lumen 500, as illustrated in FIG. 7C. A dilation catheter (e.g., a balloon catheter or stent catheter 350 shown in FIG. 5E) may be advanced over guidewire 405 to lesion 503 for treatment, and subsequent re-establishment of blood flow towards distal region 502 of arterial vessel 500.

Figure 8A:
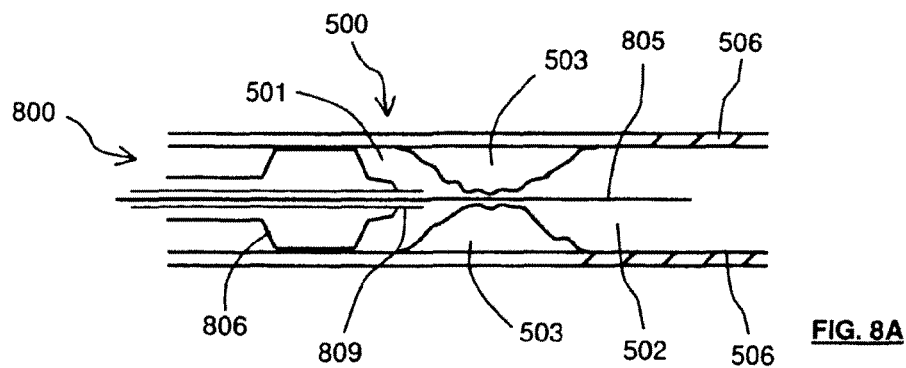
FIG. 8A illustrates another cross-sectional, side view of an expandable member to occlude blood flow near a region proximal to a lesion formed within an arterial vessel.
Figure 8B:
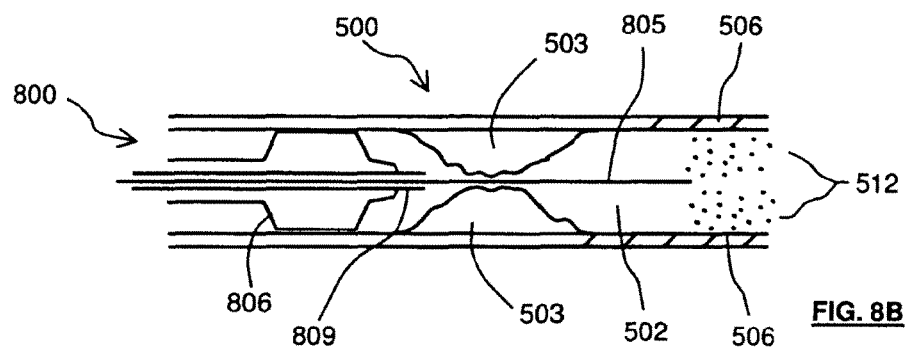
FIG. 8B illustrates an anti-reperfusion injury drug released from the guidewire for absorption by the arterial wall of the ischemic region.
Figure 8C:
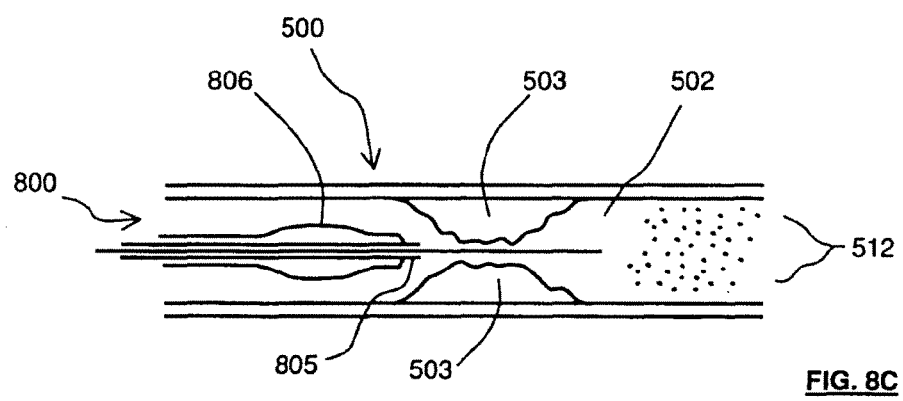
FIG. 8C illustrates the deflation of the expandable member for the removal of the device.

In an alternative embodiment, it may not be necessary for the drug delivery device to include an infusion catheter to release the drug in the region distal to the lesion. FIGS. 8A-8C illustrate another sequence of events related to an alternative method for the delivery of an anti-reperfusion injury drug in which the guidewire may be used to release the anti-reperfusion injury drug. Catheter device 800 includes a distal portion with an expandable member 806 to occlude blood flow in a region proximal 501 to lesion 503, as shown in FIG. 8A. A guidewire lumen 809 is formed within elongated catheter body 801 for the advancement of guidewire 805 past lesion 503 and towards the region distal 502 to lesion 503 (and near ischemic region 506). In one embodiment, the structure of guidewire 805 may form a lumen for passing the drug from an injection port near the proximal end of device 800 for release from the distal tip. As shown in FIG. 8B, anti-reperfusion injury drug 512 is released from guidewire 805 for absorption by the arterial wall of ischemic region 506. Expandable member 806 may then be deflated, and device 800 removed from arterial lumen 500, as shown in FIG. 8C.

As described above, embodiments of medical devices described herein have been generally described as being adapted for the delivery of anti-reperfusion injury drugs to an arterial vessel. The anti-reperfusion injury drug may be one or a combination of the following antibodies, peptides, biochemical compounds, small molecules, antisense agents that interfere specific RNA transcription, and/or decoys that interfere VCAM. The peptides may include IGF-I, Growth Hormone, BNP, estrogen, VEGF, FGF, and/or HGF. Biochemical compounds may include adenosine, adenosine, adenosine isoforms, Na/H exchange inhibitors, Na/K exchangers, NO donors, calcium channel blockers, calcium antagonists, antioxidants, and/or super-oxide scavengers. Small molecules may include those composed with active sites of the above-mentioned drugs. The antisenses and decoys may include those inhibiting the pathway involved in reperfusion signaling or preventing cell survival. The anti-reperfusion injury drugs listed may be formulated such that they are suitable for local therapy, for example, with respect to a guidewire or infusion catheter based delivery system. In one embodiment, the drug concentration may be higher relative to systemic intravenous administration.

In the foregoing specification, a medical device has been described with reference to specific exemplary embodiments thereof. For example, the medical device may be used occlusive lesions formed near the walls of an arterial vessel. It will, however, be evident that various modifications and changes may be made thereto without departing from the broader spirit and scope of the medical device as set forth in the appended claims. The specification and figures are, accordingly, to be regarded in an illustrative rather than a restrictive sense.

What is claimed is:

1. A method to prevent reperfusion injury, the method comprising:
   advancing a guidewire through a lesion and near an ischemic region distal to the lesion;
   advancing an occlusion catheter proximal to the lesion;
   occluding blood flow proximal to the lesion causing blockage of blood flow to the ischemic region distal to the lesion, wherein occluding comprises occluding blood flow proximal to the lesion, but not across the lesion or distal to the lesion; then
   delivering a therapeutic drug to the ischemic region distal to the lesion using a lumen in the guidewire; and
   treating the lesion with a dilating device to reintroduce blood flow to the ischemic region distal to the lesion, wherein the therapeutic drug is delivered before treating the lesion with the dilating device.

2. The method of claim 1, wherein delivering comprises releasing anti-reperfusion injury drug from an infusion lumen of the guidewire proximal to the ischemic region and for absorption by the arterial wall of the ischemic region.

3. The method of claim 1, wherein the occlusion catheter:
   includes a guidewire lumen formed within an elongated catheter body for the advancement of the guidewire past the lesion and towards the ischemic region distal to lesion;
   does not include an infusion catheter to release the drug in the region distal to the lesion.

4. The method of claim 1, wherein advancing further comprises:
   progressing the guidewire disposed within the infusion catheter past the lesion to the region distal to the lesion; and tracking the occlusion catheter over the guidewire to the region distal to the lesion.

5. The method of claim 1, wherein the guidewire does not increase a blood flow across the lesion.

6. The method of claim 1 wherein delivering a therapeutic drug comprises deploying an anti-reperfusion injury agent to the region distal to the lesion; and wherein treating the lesion with a dilating device comprises expanding a stent to the lesion after deploying the anti-reperfusion injury agent.

7. The method of claim 1 wherein advancing the guidewire further comprises advancing a guidewire having a diameter small enough to advance through the lesion without causing a large channel or a reperfusion pathway to form through the lesion.

8. The method of claim 1 wherein occluding blood flow comprises inflating a balloon proximal to the lesion to cause the blockage; and wherein treating the lesion with a dilating device comprises deflating the balloon, advancing the balloon to the lesion, and reinflating the balloon to treat the lesion.

9. The method of claim 1, wherein the dilating device is coupled to the occlusion catheter.

10. The method of claim 1, wherein treating further comprises one of inflating a dilatation balloon to expand the lesion, inflating the expandable member to the lesion to reintroduce blood flow to the distal region, and expanding a stent to the lesion.

11. The method of claim 1 wherein delivering the therapeutic drug comprises applying an anti-reperfusion injury drug to the region distal to the lesion for a period of time sufficient to allow the drug to infuse into an arterial wall and take effect, prior to treating the lesion with a dilating device.

12. A method to prevent reperfusion injury, the method comprising:
    advancing a guidewire having an infusion lumen within an arterial vessel from a region proximal to a lesion to an ischemic region distal to the lesion;
    delivering an anti-reperfusion injury drug from the infusion lumen to the ischemic region distal to the lesion, wherein, during delivering, only an outer surface of the guidewire is exposed through the lesion, and the exposed outer surface has a diameter small enough to advance through the lesion, and wherein blood flow is only occluded proximal to the lesion, but is not occluded across the lesion, and is not occluded distal to the lesion; and
    treating the lesion with a dilating device coupled to the infusion lumen to reintroduce blood flow to the ischemic region distal to the lesion, wherein the anti-reperfusion injury drug is delivered before treating the lesion with the dilating device.

13. The method of claim 12, wherein advancing further comprises occluding a blood flow from a region proximal to the lesion prior to delivering the anti-reperfusion drug to maintain blockage of blood flow in the region proximal to the lesion.

14. The method of claim 12, wherein treating further comprises one of inflating a dilatation balloon to the lesion, expanding a stent to the lesion, and assessing any injury to the arterial vessel by the reintroduction of blood flow to the region distal to the lesion.

15. The method of claim 12, wherein during delivering, only an outer surface of the guidewire is exposed through the lesion, and the exposed outer surface has a diameter small enough to advance through the lesion without causing a large channel or reperfusion pathway to form through the lesion.

* * * * *